US006535689B2

(12) United States Patent
Augustine et al.

(10) Patent No.: US 6,535,689 B2
(45) Date of Patent: Mar. 18, 2003

(54) IV FLUID WARMING SYSTEM WITH DETECTION OF PRESENCE AND ALIGNMENT OF CASSETTE

(75) Inventors: Scott Douglas Augustine, Bloomington, MN (US); Gary Rabindranath Maharaji, Eden Prairie, MN (US); Allen Hamid Ziaimehr, Arden Hills, MN (US); Scott Allen Entenman, St. Paul, MN (US)

(73) Assignee: Augustine Medical, Inc., Eden Prairie, MN (US)

( * ) Notice: Subject to any disclaimer, the term of this patent is extended or adjusted under 35 U.S.C. 154(b) by 0 days.

(21) Appl. No.: 09/782,808

(22) Filed: Feb. 14, 2001

(65) Prior Publication Data

US 2001/0009610 A1 Jul. 26, 2001

Related U.S. Application Data

(63) Continuation of application No. 09/265,063, filed on Mar. 9, 1999.

(51) Int. Cl.$^7$ ................................................. A61F 7/00
(52) U.S. Cl. ................................................. 392/470
(58) Field of Search ........................... 392/470, 479, 392/480; 219/518; 340/568.1, 572.5, 572.7; 604/113, 263, 114, 153, 65, 67, 46

(56) References Cited

U.S. PATENT DOCUMENTS

| 3,140,716 | A |   | 7/1964 | Harrison et al. |        |
|-----------|---|---|--------|-----------------|--------|
| 4,574,876 | A | * | 3/1986 | Aid             | 165/46 |
| 4,602,910 | A |   | 7/1986 | Larkin          |        |
| 4,731,072 | A |   | 3/1988 | Aid             |        |
| 4,847,470 | A |   | 7/1989 | Bakke           |        |
| 4,919,326 | A |   | 4/1990 | Deiger          |        |
| 5,013,889 | A |   | 5/1991 | Bakke           |        |
| 5,098,202 | A |   | 3/1992 | Rosenbaum       |        |
| 5,102,234 | A |   | 4/1992 | Levy            |        |
| 5,125,069 | A | * | 6/1992 | O'Boyle         | 392/465 |
| 5,245,693 | A |   | 9/1993 | Ford et al.     | 392/470 |
| 5,381,510 | A |   | 1/1995 | Ford et al.     | 392/470 |
| 5,423,421 | A |   | 6/1995 | Inoue et al.    |        |
| 5,520,975 | A |   | 5/1996 | Inoue et al.    |        |
| 5,733,619 | A |   | 3/1998 | Patel et al.    |        |
| 5,792,526 | A |   | 8/1998 | Watanabe et al. |        |
| 5,865,309 | A |   | 2/1999 | Futagawa et al. |        |
| 5,875,282 | A |   | 2/1999 | Jordan et al.   |        |

FOREIGN PATENT DOCUMENTS

EP 0 776 670 A2 6/1997

OTHER PUBLICATIONS

PCT Search Report For PCT/US00/04421.
Brochure for "The Medi–Temp™ II GAYMAR® Blood/Fluid Warmer", Gaymar Industries, Inc.

* cited by examiner

Primary Examiner—Teresa Walberg
Assistant Examiner—Quang Van
(74) Attorney, Agent, or Firm—Gray Cary Ware & Freidenrich; Terrance A. Meador

(57) ABSTRACT

An intravenous (IV) fluid warming system with a removable heat exchanger includes a presence detector. The system is for warming an IV fluid before infusion into a body. The system includes a warming unit for warming the IV fluid and an inlet slot for receiving a heat exchanger, preferably embodied as a cassette. The heat exchanger is sized to fit into the inlet slot of the warming unit. The heat exchanger has a heat exchanger membrane with an internal fluid pathway that is in fluid communication with a fluid inlet port and a fluid outlet port. While the heat exchanger is in the warming unit, the IV fluid flows through the internal fluid pathway of the heat exchanger, warming the fluid. A heat exchanger presence detector is part of the warming system. The presence detector detects the presence of the heat exchanger when it is received in the warming unit. The presence detector enables the heating operation of the warming unit when the presence of the heat exchanger is sensed.

36 Claims, 6 Drawing Sheets

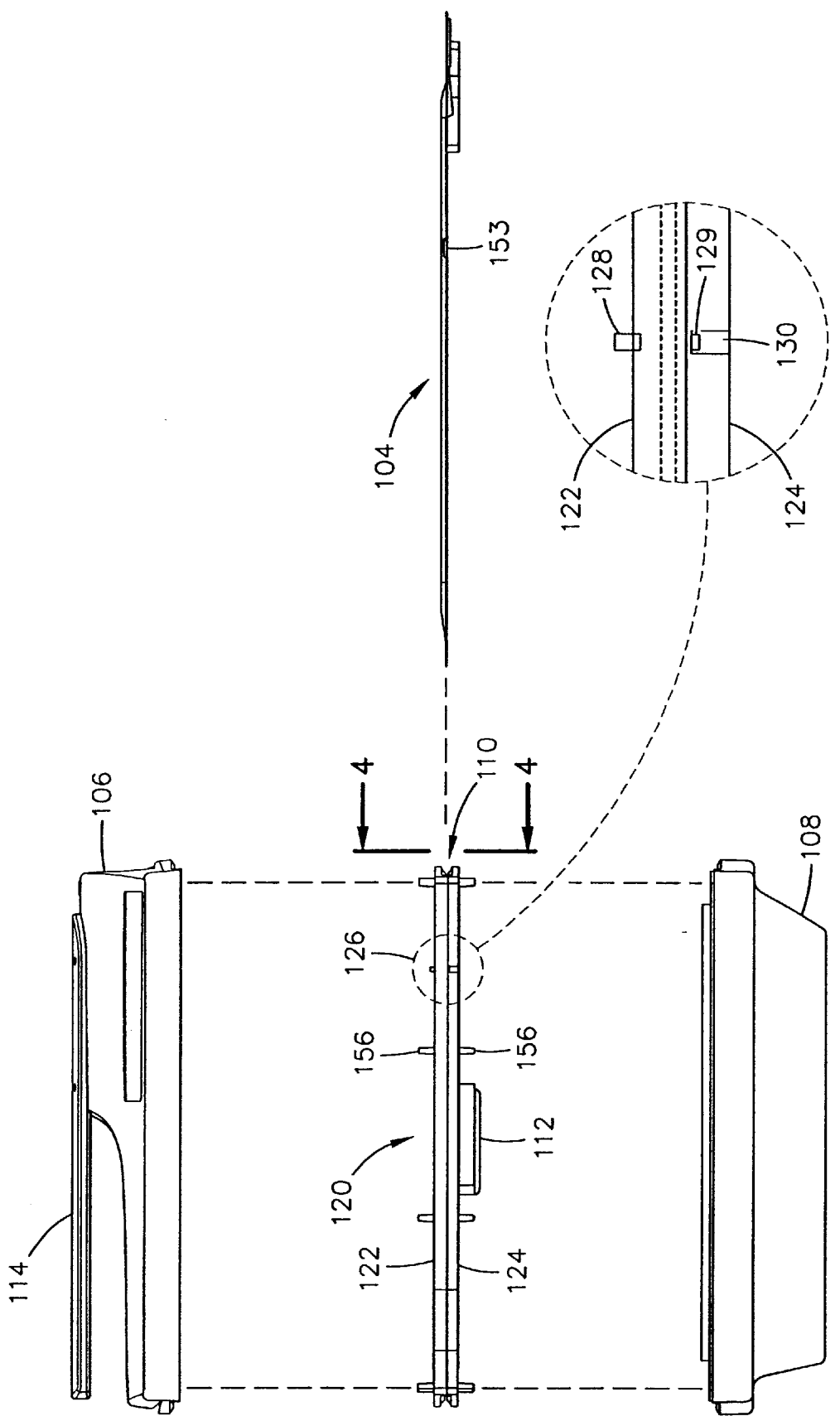

IV FLUID WARMING SYSTEM WITH DETECTION OF PRESENCE AND ALIGNMENT OF CASSETTE

This is a continuation of U.S. patent application Ser. No. 09/265,063, filed Mar. 9 1999.

BACKGROUND OF THE INVENTION

1. Field of the Invention

This invention relates generally to intravenous (W) fluid warming devices and particularly, a warming system used for warming of IV fluids prior to introduction into a body and more particularly, to an IV fluid warming system having a presence detector to detect the presence of an IV fluid warming cassette in a warming unit.

2. Description of the Related Art

Intravenous fluid infusion is a commonly used clinical technique. Since the infused fluids (also "IV fluids") are usually stored at cool temperatures to preserve freshness, they must frequently be heated before introduction into a body. For infusion of fluids into a human it may be desirable to raise the temperature of the fluid to a normal core body temperature of about 98.6 F. In other cases, other temperatures may be indicated. For example, during open heart surgery the temperature of patient is lowered to a hypothermic level; fluid must therefore be infused at the same lower temperature.

The prior art embraces systems for warming fluids as they are being infused into a body. Such systems, which may be denoted as "fluid warming" systems, have utilized a variety of means for heating fluids. Such means include heating by conduction or convection, with heat being provided by a heated fluid such as air or from an electro-resistive source such as a coil or plate. There are problems that are particular to each of these systems, especially in the clinical context. For example, one system heats fluid to be infused by conducting it through a heated fluid. Such systems typically are heavy, cumbersome, require frequent cleaning, and can pollute the clinical environment, where cleanliness is of vital importance. Typically these systems dispose a conduit in a dense fluid such as water, heat the water, and conduct the fluid to be infused through the conduit, relying upon heat to be transferred by conduction from the heated water, through the conduit to the fluid. Such systems rely upon a reservoir to contain a constant volume of heated water. This reservoir can become contaminated and proliferate undesirable bacterial agents. Therefore leaks in such systems are of particular concern in sterile settings.

In other systems, heat is transferred from an electro-resistive heating element to the fluid which is contained in a heat exchanger structure that provides a fluid pathway for the fluid to travel and a conductive pathway for thermal energy to be transferred from the heating element to the fluid. One example is an in-line fluid heating apparatus that includes an enclosure containing one or more heating elements and a cassette that is removeably received within the enclosure. The cassette defines a complex fluid flow pathway. The outline of the fluid flow pathway is preferably precisely replicated in the heating elements of the enclosure in order to maximize the "dwell time" of the fluid in the pathway thereby to maximize the potential amount of heat transferred to the fluid as it flows through the pathway in the cassette. These systems are termed "dry heat warming" systems.

Dry heat warming systems are, at this point, preferred for heating fluid to be infused. However, the dry heat warming systems that are available tend to exhibit suboptimal performance for a number of reasons. Clinical practice today indicates the desirability of providing fluid flow for intravenous infusion in a broad range of rates, from a rate sufficient to keep a vein open (KVO) up to 30,000 ml/hr. Manifestly, the transfer of thermal energy to the fluid must keep pace with the flow rate of the fluid; heat transfer must take place rapidly to heat a fluid in a high volume, rapid infusion situation. However, the rate of heating must be carefully matched to the rate of fluid flow One significant drawback of prior art dry heat warming systems is a mismatch between the rate of heating and the rate of fluid flow; sometimes the fluid is heated too rapidly, resulting in temperatures well above a desired temperature. Such over heating can damage fluids, particularly blood. Overheated blood produces hemolysis, the disintegration of red blood cells. Manifestly, the fluid warming system must well calibrate the rate of fluid flow to the rate of heating.

Calibration of fluid heating with respect to fluid flow depends on many parameters that are inherent in the construction of an insertable heat exchanger, in the shape of the fluid flow path of the heat exchanger, and in the positioning of the heat exchanger in the warming unit. Particularly, misregistration between the fluid flow path of the heat exchanger and the corresponding shape of a heating element can result in undesirable temperatures outside of a predetermined temperature range. For example, a heater plate in a warming unit might be configured in such a manner as to vary the rate at which heat is conducted to the fluid pathway. In this regard, the heater might deliver a greater amount of heat at the inlet of the fluid pathway than at the outlet. In such a case, an accidental reversal of the heat exchanger in the heating unit would almost certainly result in improper heating of the fluid. Similarly, if control of the warming unit depends upon a heat sensing element disposed at a particular location with respect to the heat exchanger, accidental reversal could result in a erroneous control of the warming unit and improper heating of the fluid. Such reversal is entirely possible in the case of cassette that may inserted into and removed from a warming unit.

Typically, dry heat fluid warming systems capable of heating hydrating fluids within a broad temperature range may be burdened with sophisticated and expensive functional and mechanical hardware to ensure proper operation. In a warming system where the design and construction of a removable heat exchanger are precisely optimally matched to the design, construction, and performance of the warming unit, any provision to ensure proper orientation between the heat exchanger and the warming unit would improve the efficiency, safety, and cost of the system.

From the discussion above, it should be apparent that there is a need for an in-line IV fluid warming system of the type including a removable heat exchanger and a warming unit that can heat IV fluids quickly, efficiently and consistently, without damaging the fluid, for immediate and safe use with a patient. Importantly, such a system should guarantee correct alignment between the heat exchanger and heating elements in the warming unit. This invention satisfies these needs.

SUMMARY OF THE INVENTION

Broadly, the present invention concerns the warming of an IV fluid during infusion into the body of a person or animal: Typically, IV fluid (including blood) is stored at low temperatures to prolong its freshness. Before use, it must be warmed. During emergencies and certain surgical procedures, the fluid must be warmed quickly. The present invention allows the IV fluid to be warmed in line as it flows from an IV reservoir to a person.

This invention is an intravenous (IV) fluid warming system having a warming unit that receives an insertable heat exchanger, preferably embodied as a cassette. A presence detection circuit renders the warming unit inoperative when the cassette is not in place, when the cassette is inserted incorrectly, or when an incompatible cassette is present.

In a preferred embodiment, the warming unit comprises an enclosure supporting a heater plate assembly. The heater plate assembly has an opening inlet into which the cassette may be inserted. The heater plate assembly includes a first heater plate positioned on one side of the inlet and a second heater plate positioned on an opposing side of the inlet, such that when the cassette is positioned in the warming unit, the first heater plate is positioned on one side of the cassette and the second heater plate is positioned on an opposing side of the cassette. Operation of the heater plate assembly is enabled in response to an indication by the presence detection circuit that the cassette has been correctly seated in the inlet. In an illustrative example of the presence detection circuit, a magnet is located on or in the first heater plate and a sensor is located on or in the second heater plate so as to be able to detect the magnet, the magnet and sensor being separated by the width of the inlet slot. A presence indicator is positioned on a cassette such that when the cassette is properly inserted into the warming unit, the presence indicator is disposed between the magnet and the sensor, disabling the sensor with respect to the magnet, and enabling the warming unit to operate the heater plates.

Other features and advantages of the present invention should be apparent from the following description of the preferred embodiments, which illustrate, by way of example, the principles of the invention.

BRIEF DESCRIPTION OF THE DRAWING

FIG. 2 is an exploded side view of FIG. 1 showing components of the warming unit;

FIG. 3 is an enlarged view showing details of a portion of a cassette presence detection switch;

DESCRIPTION OF THE PREFERRED EMBODIMENTS

Figure 1:
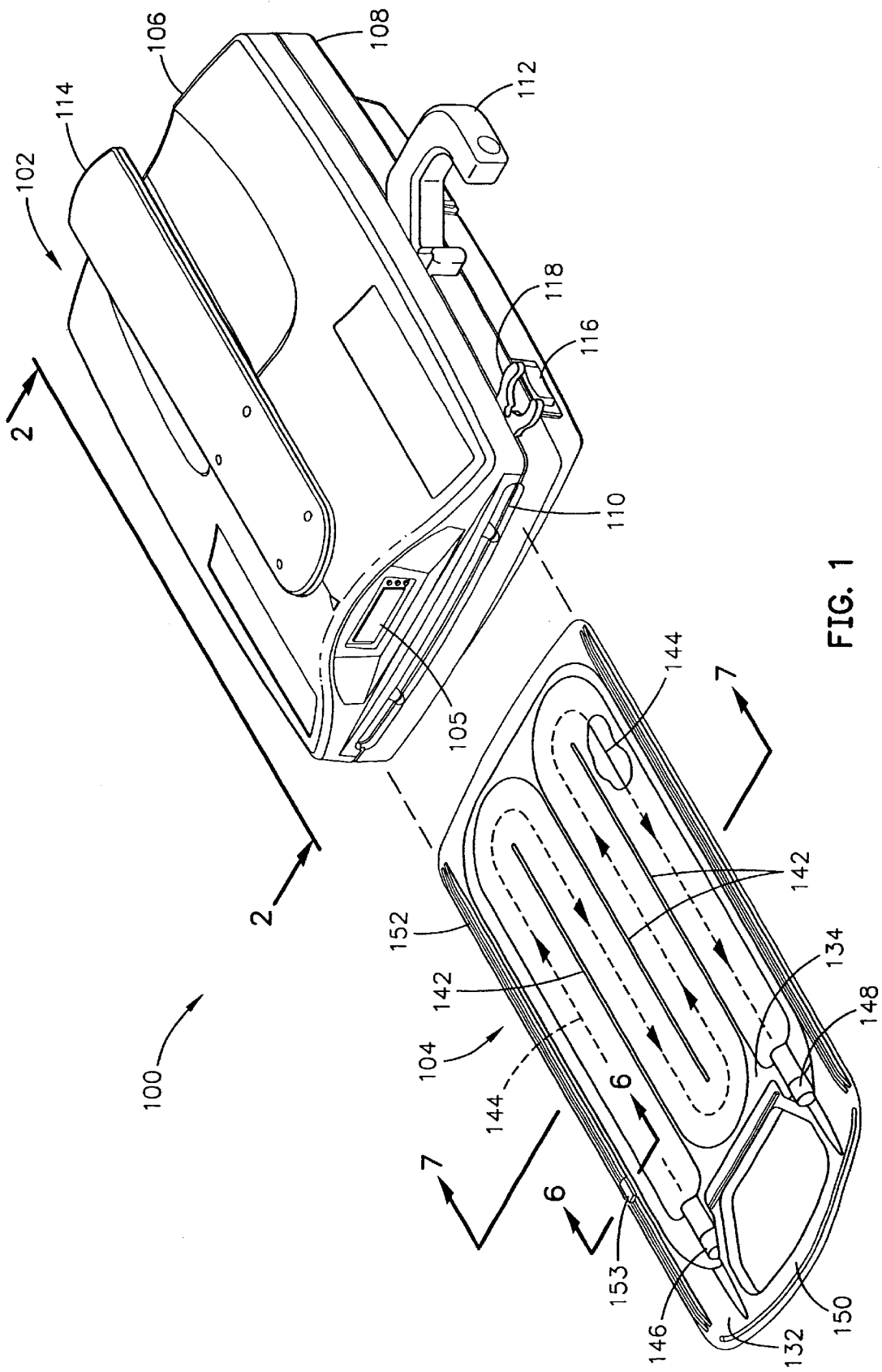
FIG. 1 is a perspective view showing an embodiment of the present invention in an intravenous (IV) fluid warming system utilizing a warming unit with an insertable heat exchanger, preferably embodied as a cassette.

FIG. 1 illustrates an embodiment of this invention, in the form of an intravenous (IV) fluid warming system ("system") 100. The IV fluid warming system 100 includes a warming unit 102 and a heat exchanger, preferably in the form of a cassette 104. In use, the cassette 104 is inserted into the warming unit 102. Once inserted, a presence detector (described below) senses the presence and correct orientation of the cassette 104 in the warming unit 102, enabling heating elements in the warming unit, 102 to apply heat to the cassette 104. During operation of the system 100, an IV fluid reservoir such as a bag is attached to a fluid inlet line, allowing the IV fluid to flow into an inlet port and through an internal fluid pathway of the cassette 104. Heating elements in the warming unit 102 warm the IV fluid as it travels through the internal fluid pathway of the cassette 104. The IV fluid exits the cassette 104 though a fluid exhaust port and is delivered for use. Details of the IV fluid warming system 100 will now be described.

Referring again to FIG. 1, the system 100 has at least two components, the warming unit 102 and the cassette 104. The warming unit 102 has a first (upper) enclosure 106 and a second (lower) enclosure 108. An inlet slot 110 is located in the warming unit for receiving the cassette 104. The warming unit 102 may also have a clamp 112 for attaching the warming unit 102 to an IV support pole, a handle 114 for carrying, an on/off switch 116 and a bubble trap receiver 118.

FIG. 2 is an exploded view of FIG. 1 showing the first enclosure 106 with handle 114 and the second enclosure 108. Disposed between the first and second enclosures 106 and 108 is a heater plate assembly 120 that is capable of receiving the cassette 104. The heater plate assembly 120 consists of a first heater plate 122 and a second heater plate 124 with an opening between them forming the inlet slot 110 for receiving the cassette 104. In the preferred embodiment, the heater plates are heated using electrically resistive heaters. The heater plate assembly 120 may also employs other heating methods such as steam coils, condensing heat pipes, quartz lamps, hot air or other equivalent modes of heating. The heater plate assembly 120 also contains components of a cassette presence circuit 126 (shown in FIGS. 9 and 10). In one embodiment shown in FIG. 3, a portion of the cassette presence circuit 126 comprises a magnet 128 located on or in the first plate 122 and a sensor 129 located in a slot 130 in the second plate 124. The operation of the cassette presence circuit 126 is described below. A controller 105 is also enclosed in the warming unit 102 to monitor the functions of the warming unit 102. The controller 105 controls the level of operation and other functions of the heater plate assembly 120. The controller 105 may be connected to the on/off switch 116 and the cassette presence circuit 126.

In other embodiments discussed in more detail below, the cassette presence may be sensed by other types of switches including, but not limited to, electrical, radio frequency, magnetic, optical, pressure, and/or mechanical switches. It is envisioned that the switch may be located in the warming unit and activated by the side rails of the cassette when inserted in the warming unit. The rails may have a ridge or indent corresponding to the switch to activate it. In another embodiment, the switch may be located deep inside the warming unit, opposite the opening such that the switch is activated when the cassette is fully inserted in the warming unit.

Figure 4:
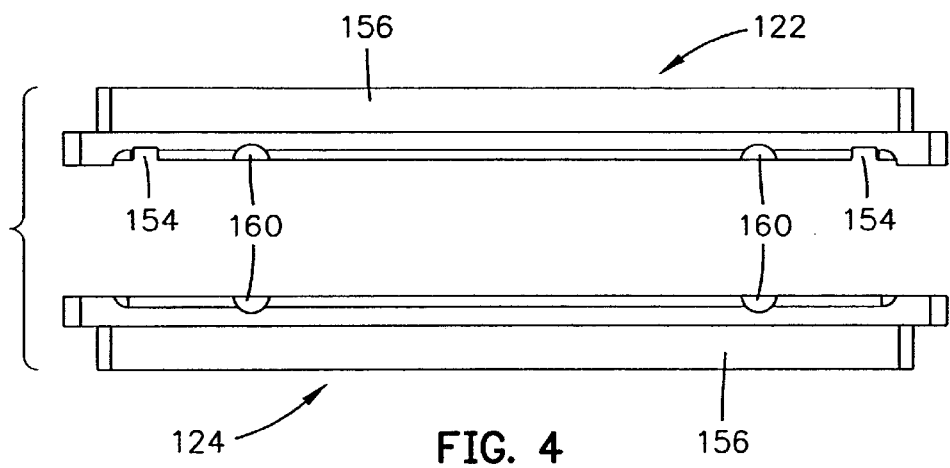
FIG. 4 is an exploded front view of a heater plate assembly in FIG. 2, showing slots and tubing reliefs in heater plates of the heater plate assembly.
Figure 5:
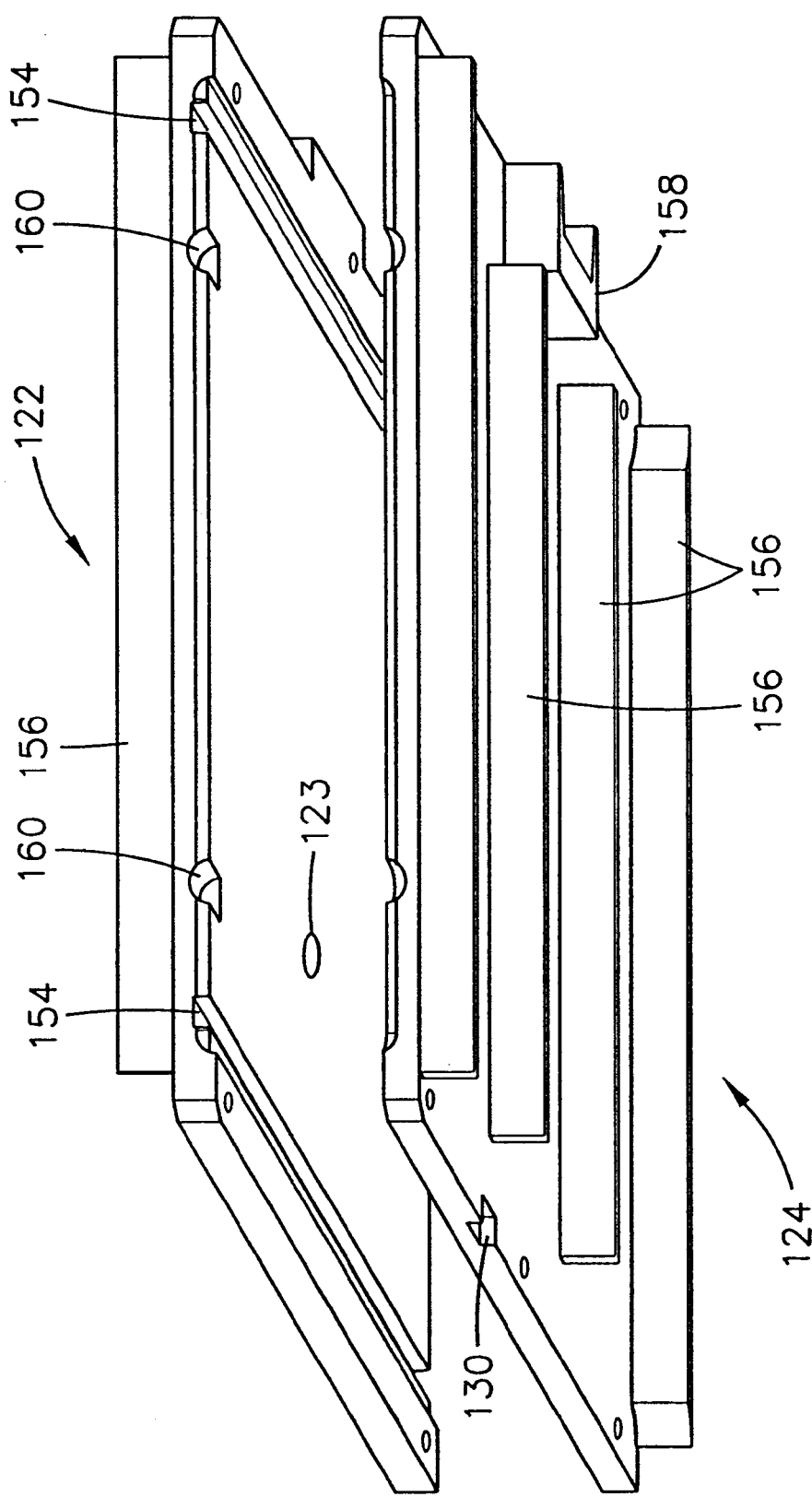
FIG. 5 is an exploded perspective view of FIG. 4.

FIG. 4 is an exploded front view showing the first heating plate 122 and the second heating plate 124 of the heater plate assembly 120. A number of slots 154 are located in the first heater plate 122 and are used to guide and align the heat exchanger cassette 104 as it enters the inlet slot 110. The inlet slot 110 may extend the full length of the heater plate assembly, allowing for an open pathway to facilitate cleaning and maintenance of the heating assembly. Additionally, a number of reliefs 160 are formed in the heating plates 122, 124 to allow room for IV fluid inlet and outlet tubes when the heat exchanger cassette 104 is positioned in the warming unit 102. FIG. 5 shows an exploded perspective view looking up at the heater plate assembly 120. The slots 154 can be seen extending the length of the first heater plate 122. Also seen is the slot 130 in the second heater plate 124 wherein the sensor 129 is disposed. Additionally, a number of ribs 156 are on both of the heater plate sides 122, 124 to enhance the structural and thermal properties of the plates. A thermocouple, RTD, or other appropriate thermal sensing device 123 can be placed in one or more of the heater plates for sensing the temperature of an inserted heat exchange cassette. A reinforced area 158 is used for the clamp 112.

Figure 6:
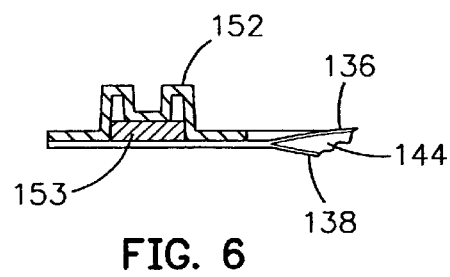
FIG. 6 is a sectional view taken along 6—6 of FIG. 1 showing a frame rail and presence indicator on the heat exchanger.
Figure 7:
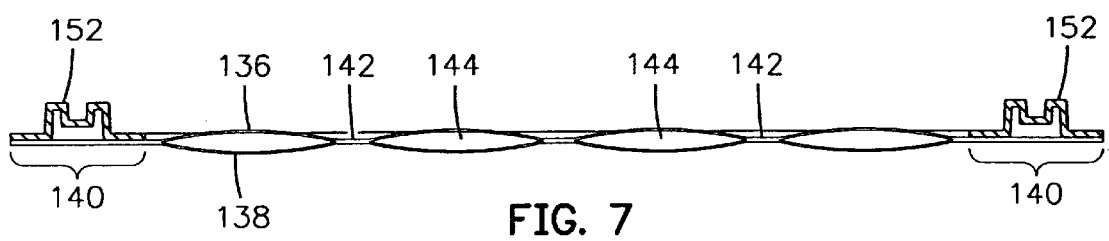
FIG. 7 is a sectional view taken along 7—7 of FIG. 2 showing details of the heat exchanger.

Referring again to FIG. 1, the cassette 104 is shown. The cassette 104 is made of a frame 132 surrounding a heat exchanger membrane 134. Located at one end of the frame is a handle 150. Along the sides of the frame 132 are a pair of extending rails 152. The rails 152 are sized to slidably fit into the slots 154 of the warming unit 102. FIG. 6 is an enlarged cross-sectional view of one portion of the rail 152 showing a presence indicator 153 that functions in conjunction with the cassette presence circuit 126. The presence indicator 153 may be made from a soft ferro-magnetic material, for example. The frame may be made from a non-magnetic material that is inert to IV fluids. One such material is vacuum formable plastic such as polyvinyl chloride (PVC). FIG. 7 shows a cross-sectional view of the heat exchanger membrane 134. The heat exchanger membrane 134 consists of a first layer 136 and a second layer 138 joined together in a substantially continuous seam 140 around their perimeters along a side of frame 132. Along with being joined by the seam 140, the upper first and second layers 136, 138 may also be joined together at one or more locations 142 within the seam 140 creating an internal serpentine fluid pathway 144 (see FIG. 7 and dashed line in FIG. 1). In the preferred embodiment, the first and second layers 136, 138 are made of a non-magnetic, high temperature, biocompatible, thermoplastic material capable of withstanding the heat generated inside the warming unit 102. The layers are configured such that the heat transfer properties permit the heat exchanger cassette to operate within the fluid temperature output parameters of the system. For example, a flexible PVC thermoplastic material having a substantially uniform thickness of 4 mil has a known thermal conductivity, capable of consistently transferring a determinable amount of heat to the internal fluid pathway. The layers may be joined by adhesive or thermal bonds, for example. A fluid inlet port 146 is positioned at the beginning of the internal fluid pathway 144, allowing the IV fluid into the fluid pathway 144. At the end of the internal fluid pathway 144 is a fluid outlet port 148. The fluid outlet port 148 also may have an infrared thermometer, integral heat sensor, or thermocouple for sensing fluid temperature. Other heat sensors or thermocouples may be placed at other locations in the system such as at the inlet port 146 or may be strategically located inside the fluid pathway 144. The cassette 104 may either be disposable or may be sterilized between uses.

Figure 8:
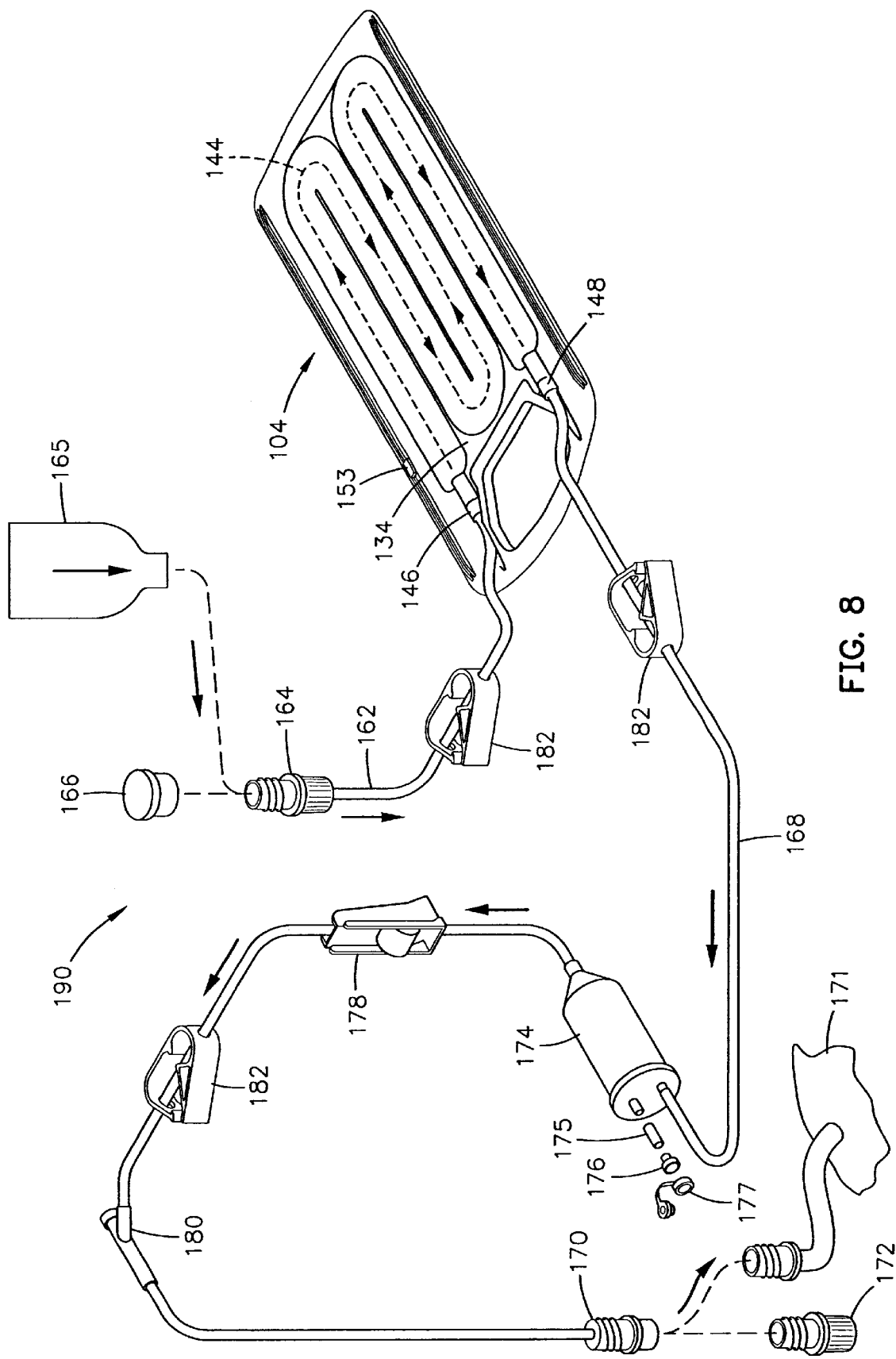
FIG. 8 is a perspective view of the heat exchanger.

FIG. 8 shows a heat exchanger cassette assembly ("cassette assembly") 190 which includes the cassette 104 and an attachment apparatus. A fluid inlet line 162 is used to carry fluid to the heat exchanger membrane 134. One end of the fluid inlet line 162 may be attached to the fluid inlet port 146, while the opposite end has a luer connector 164 that is compatible with a standard IV blood/fluid bag 165 or infusion set. When not attached to an IV bag, a vented cap 166 may be attached to the luer 164. A fluid outlet line 168 may be attached to the fluid outlet port 148 with the opposite end having a luer 170 for attachment to a person 171. When not so attached, a vented cap 172 may be placed on the luer 170. As is common when infusing IV fluids, a bubble trap 174 may be positioned in the fluid line 168. The bubble trap 174 includes a connector 175, a vent 176 and a vent cap 177. While the heat exchanger cassette 104 is positioned in the warming unit 102, the bubble trap 174 may be held in the bubble trap receiver 118. A roller clamp 178 may also be positioned on the fluid outlet line 168 to control the flow rate of the IV fluid. Additionally, the fluid outlet line 168 may include a "y" injection site 180 for the introduction of other fluids or drugs into the patient. Pinch clamps 182 may also be used to control the IV fluid flow.

Figure 9:
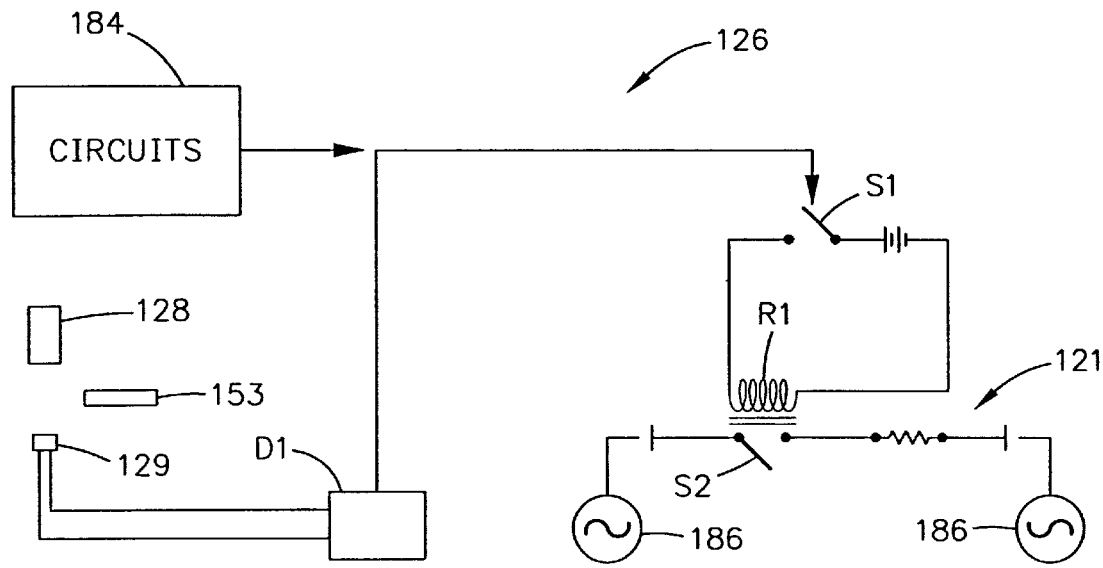
FIG. 9 is a schematic of a cassette presence detection circuit showing a first circuit arrangement when the presence indicator is not registered with the circuit.
Figure 10:
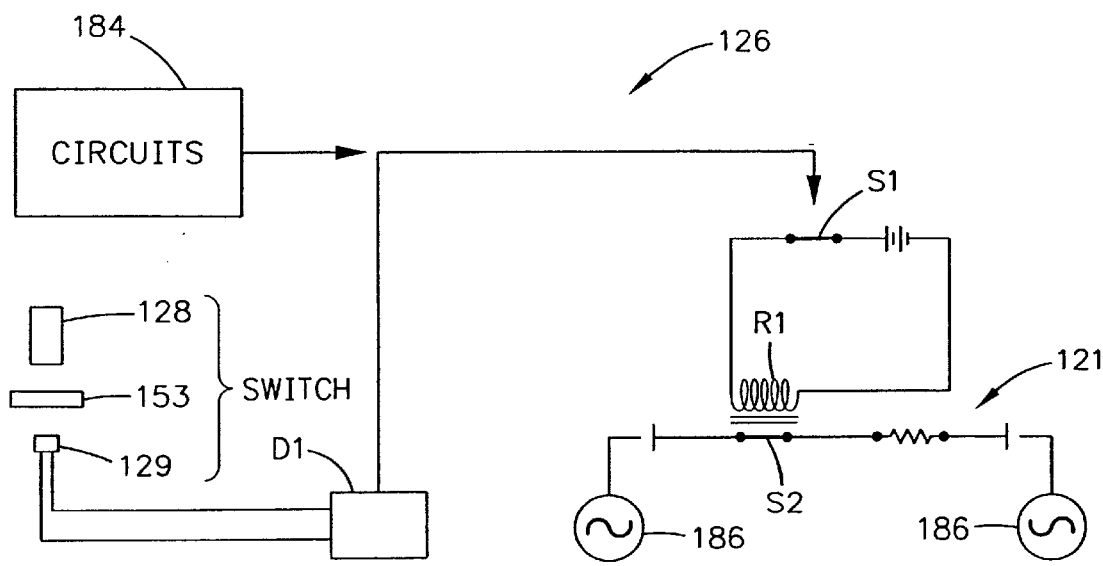
FIG. 10 is a schematic of the cassette presence detection circuit showing a second circuit arrangement when the presence indicator is registered with the circuit.

FIGS. 9 and 10 show schematic diagrams of a cassette presence sensing circuit 126 that may be incorporated within the warming unit 102. The cassette presence circuit 126 includes first circuit elements 128 and 129 (already described), switch driver D1, switch S1, relay R1, and a second circuit element 153 (already described). The first circuit elements are located in or on the housing of the warming unit 102. The second circuit element is mounted on the cassette 104. The presence circuit elements 128, 129, and 153 operate cooperatively to indicate receipt of the cassette 104 in the warming unit. A heater circuit 121 includes a switch S2, driven by the relay R1. When S1 is open, relay R1 is inactive and switch S2 is open. When switch S1 is closed, the relay R1 is activated, closing switch S2.

FIG. 9 shows the cassette presence circuit 126 when the cassette 104 is not inserted or is not properly aligned in the warming unit 102. When the cassette 104 is not present in the warming unit 102 or is out of position, the sensor 129 detects the magnet 128. By detecting the magnet 128, the switches S1 and S2 are held open by the switch drive D1 and relay R1 and will not allow the heater circuit 121 to close, disabling the heater assembly 120 from heating the first and second heater plates 122, 124. For the cassette presence sensing circuit 126 to close, the presence indicator 153 must be positioned between the magnet 128 and the sensor 129. FIG. 10 illustrates the cassette 104 inserted in the warming unit 102. When the presence indicator 153 is in position between the magnet 128 and the sensor 129, the switches S1 and S2 close, enabling the heating circuit 121 to function and heat the first and second heater plates 122, 124. In the present example, the heater circuit 121 is powered by AC current source 186. In this configuration, the cassette pressure circuit 126 controls warming unit operation by switching AC power to the warming unit in such a manner as to power the warming unit on when the cassette 104 is properly inserted and to turn the power off otherwise.

It is contemplated by the inventors that the presence sensing circuit may act on other components in the system as well. For instance, instead of enabling the heater circuit, the presence sensor may act upon a control relay that would enable a thermal sensing circuit allowing the controller to begin to operate the heaters. In another embodiment of the presence-sensing circuit, element 153 may be a passive electromagnetic element such as a coil and the sensor 129 a radio frequency transceiver. In this case the presence of the cassette will be detected by the resonance frequency of the electromagnetic element 153. Element 153 may also include an integrated circuit with embedded data which, when interrogated by the sensor 129 it will transfer the recorded data present on the circuit 153 to the sensor 129. The cassette presence sensing circuit 126 may be made of other types of circuits or switches known in the art, such as: an optical switch where the cassette interrupts a light beam, or where a hole in the cassette allows a light beam through; a mechanical switch that the cassette hits or activates when it is properly, inserted into the warming unit; or other types of electrical, magnetic, optical, and/or mechanical switches.

Thus the cassette presence sensing circuit 126 may be considered a safety measure in that the warming unit 102 cannot function without the cassette 104 in a predetermined position. Optionally, an alarm 184 may be connected to the cassette presence sensing circuit 126 to provide various indications during operation of the warming unit 102. Some examples that might cause the alarm to sound in a way to indicate the presence or absence of the cassette in the warming unit, the temperature of the warming unit or the fluid exceeding limits set by the controller, interruption of fluid flow through the cassette, or the expiration of time intervals. The cassette 104 may either be provided as a heat exchanger cassette assembly 190 (i.e., heat exchanger cassette 104 and the apparatus shown in FIG. 8) or may be assembled from individual components available to the user. It is envisioned that the inlet and outlet ports 146, 148 of the cassette 104 are of the size and shape to interface with standard fluid lines used to deliver IV fluids. To assemble the cassette assembly 190, a fluid inlet line 162 is attached to the fluid inlet port 146 of the cassette 104 by a frictional fit, with an adhesive, or some other suitable attachment means. The opposite end of the fluid inlet line 162 is attached to a standard IV bag 165 with a luer connector 164. A fluid outlet line 168 is attached to the fluid outlet port 148 by frictional fit, adhesive, or other attachment means with the opposite end having a luer that connects to infusion system of the patient. Both fluid lines are made from standard tubing material generally used for IV fluid delivery. Optionally, the fluid lines may be unique to the device and have traditional end luers to interface with common components. The fluid outlet line 168 may also contain a bubble trap 174, roller clamp 178 and "y" adapter 180. Additionally, pinch clamps 182 may be used to control the flow of fluid. The heat exchanger cassette assembly 190 (i.e., heat exchange cassette 104 with attached apparatus) is now ready to use.

In use, the cassette 104 is inserted into the inlet slot 110 of the warming unit 102. Before activation of the heating elements in the warming unit 102, the presence detection circuit 126 must detect the presence of the cassette 104 in the warming unit, as may be indicated when the presence indicator 153 in the cassette 104 is positioned between the magnet 128 and the sensor 129 in the warming unit 102. If used, the bubble trap 174 may be attached to the bubble trap receiver 118. The luer connector 164 of the fluid inlet line is attached to the IV fluid bag 165. The luer connector 170 of the fluid outlet line is attached to the patient 171. The electronic controller is programmed with the desired fluid temperature settings and the warming system is ready for operation. Relevant information such as temperature settings, current temperature, on/off status, cassette presence, and other information required for operation of the unit may be displayed by the controller 105. If desired, the warming unit 102 may be attached to an IV pole or equivalent structure. The warming unit 102 may also be carried by the handle 114 or placed on a table top in use. Once the warming unit 102 is activated, the IV fluid flows from the IV fluid bag, through the fluid inlet line 162 and inlet port 146 into the exchanger membrane 134. At this point, the exchanger membrane 134 is positioned between the first heater plate 122 and the second heater plate 124. As the IV fluid flows through the internal serpentine fluid pathway 144 it is warmed by the heating plates 122, 124. The now warmed IV fluid exits the pathway through the fluid outlet port 148 and the fluid outlet line 168 and is ready to be infused into a patient.

The rate of warming of the IV fluid may be managed according to a variety of methods. In one method, the fluid warming temperature may be managed using the controller. The controller may be attached to a plurality of temperature sensors strategically located in the warming unit. The controller would monitor, for example, the exit temperature of the warmed IV fluid and adjust the warming plates 122, 124 accordingly to keep the temperature in a predefined range. This information may be viewed in the controller display window 105. According to another method of temperature control flow of the IV fluid through the warming unit may be adjusted while keeping the temperature of the warming plates 122, 124 constant. In this method, once the warming unit is turned on, the heating plates 122, 124 are warmed to a predefined temperature. The exit temperature of the warmed fluid at the exit port 148 is monitored by a temperature sensor located near the fluid outlet port 148 and the temperature shown in the display window 105. If the fluid needs to be warmer, the fluid flow is slowed so that it spends more time in the internal serpentine fluid pathway 1.44 between the heating plates 122, 124. This slowing of the fluid can be accomplished using the roller clamp 178 or an equivalent device such as a automated flow device. If the fluid is too warm, the flow will be increased through the unit so the fluid spends less time warming.

While the invention herein disclosed has been described by means of specific embodiments and applications thereof, numerous modifications and variations could be made thereto by those skilled in the art without departing from the scope of the invention set forth in the claims.

What is claimed is:

1. An intravenous (IV) fluid warming system comprising:
   a warming unit with an inlet slot and a heater plate assembly;
   a heat exchanger receivable in the warming unit inlet slot and seatable in the heater plate assembly, the heat exchanger having an internal fluid pathway and a fluid inlet port and a fluid outlet port in fluid communication with the internal fluid pathway; and
   a sensor acting between the heater plate assembly and the heat exchanger to sense the presence of the heat exchanger in the heater plate assembly.

2. The system of claim 1, wherein the sensor comprises:
   a first circuit element in the warming unit;
   a second circuit element on the heat exchanger, the second circuit element cooperating with the first circuit element to enable a signal representing a condition between the heat exchanger and the warming unit.

3. The system of claim 2 further including;
   an indicator connected to the first circuit element for giving an indication of the condition.

4. The system of claim 3, wherein the indication is of receipt of the heat exchanger in the warming unit.

5. The system of claim 1, wherein the sensor includes a magnetic switch comprising:
   a sensor and a magnet in the warming unit with a gap between them; and
   a presence indicator on the heat exchanger sized to fit within the gap between the magnet and sensor.

6. The system of claim 1, wherein the sensor includes a mechanical switch located on the warming unit to be engaged by the heat exchanger when the heat exchanger is in the warming unit.

7. The system of claim 1, wherein the sensor includes an electronic switch having a sensor located in the warming unit to sense the heat exchanger when the heat exchanger is in the warming unit.

8. The system of claim 1, wherein the sensor includes a radio frequency transceiver in the warming unit and a passive transmitter in the heat exchanger to sense the heat exchanger when the heat exchanger is in the warming unit.

9. The system of claim 1 wherein heat exchanger comprises;
   a frame; and
   a heat exchanger membrane attached to the frame:
   a first layer of heat exchanger membrane; and
   a second layer of the heat exchanger membrane joined to the first layer by a substantially continuous seam around the peripheries of the layers.

10. The system of claim 9, wherein the first layer and second layer are made of a thermoplastic material and are joined by a thermal bond.

11. The system of claim 9 further comprising:
    the first layer also being joined to the second layer at a plurality of locations within the substantially continuous seam, forming an internal fluid pathway with a plurality of connected channels.

12. The system of claim 10, wherein the internal fluid pathway is serpentine in shape.

13. The system of claim 9 further comprising:
    a fluid inlet port in fluid communication with a first end of the internal fluid pathway;
    a fluid inlet line having a first end in fluid communication with the fluid inlet port and a second end connectable to an IV fluid container;
    a fluid exit port in fluid communication with a second end of the internal fluid pathway; and
    a fluid outlet line having a first end in fluid communication with the fluid outlet port and a second end connectable with a patient infusion system.

14. The system of claim 9, the frame including a handle.

15. The system of claim 1 further comprising:
    an attachment means for attaching the warming unit to an IV pole.

16. The system of claim 15, wherein the attachment means is a clamp.

17. The system of claim 1, wherein the heater plate assembly comprises:
    a first heater plate positioned on one side of the inlet slot; and
    a second heater plate positioned on an opposite side of the inlet slot.

18. The system of claim 1, wherein the heat exchanger is a disposable cassette.

19. The system of claim 1 further comprising:
    a warming unit controller; and
    a controller display window connected to the warming unit controller.

20. The system of claim 18 further comprising:
    a thermocouple positioned in the warming unit.

21. The system of claim 19 wherein the thermocouple is in communication with the warming unit controller.

22. An intravenous (IV) fluid warming system comprising:
    a warming unit with:
       an enclosure having an inlet slot; and, at least one heating element positioned in the enclosure; and,
    a heat exchanger comprising;
       a frame receivable in the inlet slot,
       a heat exchanger membrane attached to the frame, the heat exchanger membrane having an internal fluid pathway;
       a fluid inlet port near a first end of the internal fluid path;
       a fluid outlet port near a second end of the internal fluid path; and
       a presence detector acting between the heat exchanger and the at least one heating element.

23. The system of claim 22; wherein the enclosure comprises a first enclosure portion with a handle and a second enclosure portion.

24. The system of claim 22, wherein the presence detector comprises:
    a first circuit element in the warming unit;
    a second circuit element positioned on the heat exchanger, the second element cooperative with the first circuit element to enable a signal representing a condition between the heat exchanger and the warming unit.

25. The system of claim 24 further including;
    an indicator connected to the first circuit element for giving an indication of the condition.

26. The system of claim 25, wherein the indication is of receipt of the heat exchanger in the warming unit.

27. The system of claim 24, wherein the first circuit element includes a sensor.

28. The system of claim 27, wherein the first circuit element further includes a mechanical switch connected to the sensor and the second circuit element includes a switch contactor.

29. The system of claim 22, wherein the presence detector is a magnetic switch having a magnet near one side of the inlet slot, a sensor near another side of the inlet slot and a controller connected to the sensor.

30. The system of claim 22 further comprising:
    a warming unit controller; and
    a controller display window connected to the warming unit controller.

31. The system of claim 30 further comprising:
    a thermocouple positioned in the warming unit.

32. The system of claim 22 wherein the thermocouple is in communication with the warming unit controller.

33. A heat exchanger for being received in a warming unit for being warmed therein, comprising:
    an IV fluid cassette with an internal fluid pathway; and
    a presence indicator element on the cassette,
    wherein the presence indicator comprises a magnetic material.

34. A heat exchanger for being received in a warming unit for being warmed therein, comprising:
    an IV fluid cassette with an internal fluid pathway; and
    a presence indicator element on the cassette,
    wherein the presence indicator comprises a void in the cassette.

35. A warming unit with an opening for receiving an IV fluid heat exchanger to be warmed by the warming unit, comprising:
    an enclosure;
    a heat exchanger warming assembly in the enclosure; and a heat exchanger presence detector circuit in the enclosure, connected to the warming assembly.

36. The system of claim 35, wherein the presence detector comprises:

a first magnetic element in the warming unit; and
a second magnetic element in the heat exchanger.

* * * * *

UNITED STATES PATENT AND TRADEMARK OFFICE
CERTIFICATE OF CORRECTION

PATENT NO.   : 6,535,689 B2
DATED        : March 18, 2003
INVENTOR(S)  : Augustine et al.

It is certified that error appears in the above-identified patent and that said Letters Patent is hereby corrected as shown below:

<u>Column 11,</u>
Line 3, change "system" to -- warming unit --

Signed and Sealed this

Twenty-second Day of July, 2003

JAMES E. ROGAN
*Director of the United States Patent and Trademark Office*